United States Patent [19]

Teass, Jr., Horace A.

[11] 4,181,880
[45] Jan. 1, 1980

[54] LINEAR GROUND CONDUCTIVITY MEASURING SYSTEM

[76] Inventor: Horace A. Teass, Jr., 36 Highland Ter., Pleasantville, N.Y. 10570

[21] Appl. No.: 889,091

[22] Filed: Mar. 22, 1978

[51] Int. Cl.² ............................................. G01N 27/42
[52] U.S. Cl. .................................... 324/439; 324/425
[58] Field of Search ........... 204/195 R; 324/29, 30 R, 324/30 B

[56] References Cited

U.S. PATENT DOCUMENTS

| | | | |
|---|---|---|---|
| 3,867,687 | 2/1975 | Gealt | 324/30 R |
| 3,953,790 | 4/1976 | Ebling | 324/30 R |
| 3,965,414 | 6/1976 | Teass | 324/30 R |
| 3,993,945 | 11/1976 | Watmoth | 324/30 R |
| 4,028,618 | 6/1977 | Teass | 324/30 R |

Primary Examiner—M. Tokar
Attorney, Agent, or Firm—Peck & Peck

[57] ABSTRACT

A circuit for monitoring the conductivity of a solution has a conductivity cell with a grounded cell electrode that is operated at a distance from the reading station. A shielded cable houses the signal carrying conductors and the free end of the cable shield is purposely not grounded.

3 Claims, 1 Drawing Figure

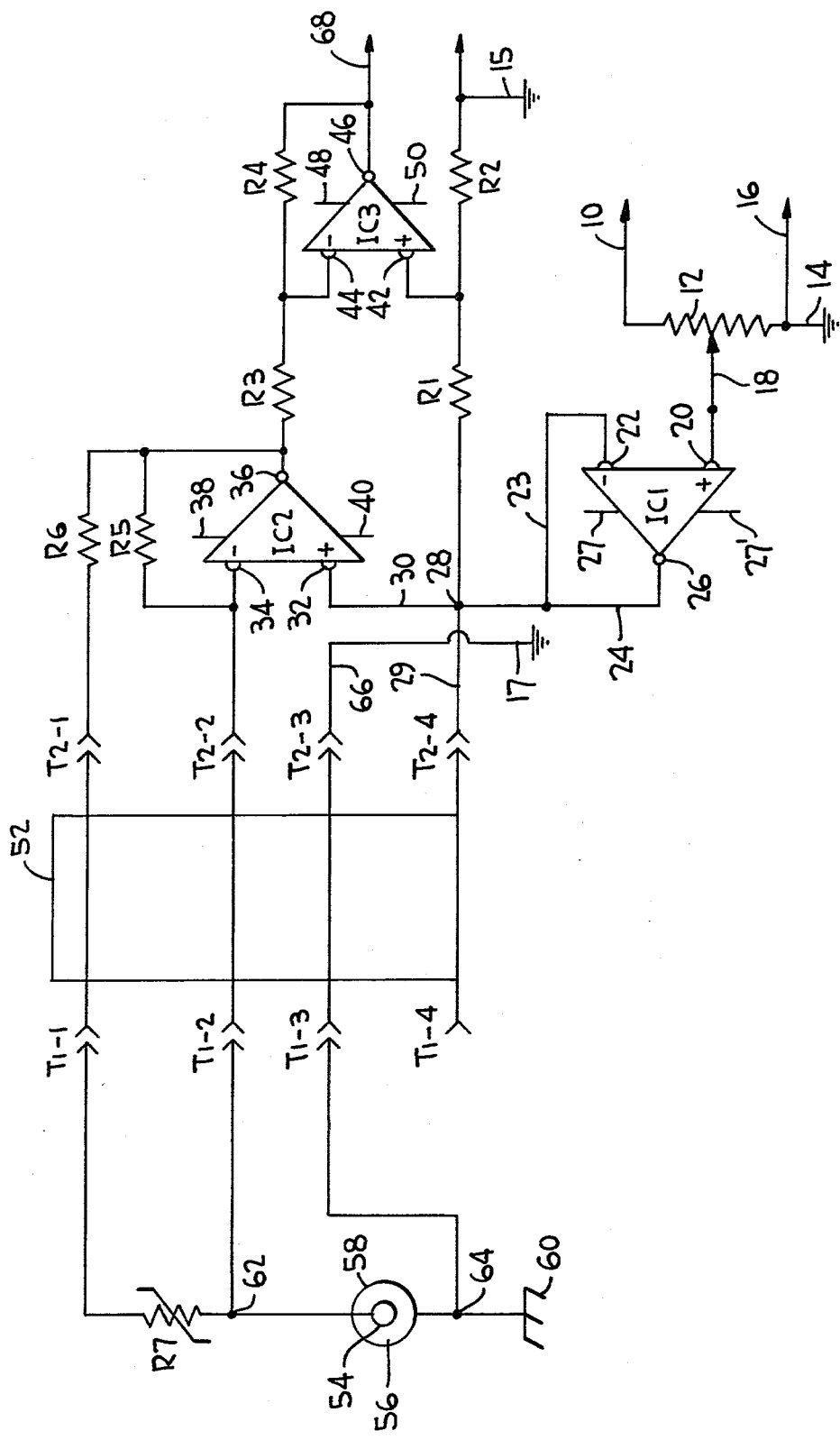

LINEAR GROUND CONDUCTIVITY MEASURING SYSTEM

BACKGROUND OF THE INVENTION

The present invention relates generally to monitoring systems and, more particularly, to a circuit for measuring the conductivity of fluids.

Industrial conductivity cell systems for the measurement of fluid conductivity are well known in the art. Typically, such systems involve the use of a conductivity cell having one of the wetted probes directly grounded and the location of the cell is at a relatively long distance from the reading station. It is often required that these industrial systems provide a conductivity signal that is directly or linearly proportional to the conductivity of a subject fluid but which remains constant in valve as the fluid changes temperature. Unfortunately, an undesirable capacitive effect introduced by the circuit elements connecting the cell to the reading station loads down the signal as it is transmitted to and from the cell and causes a significant error in the conductivity measurement.

SUMMARY OF THE INVENTION

Accordingly, it is an object of the present invention to provide a circuit for measuring the conductivity of fluids that permits the cell to be operated at an increased distance from the reading station without introducing signal error caused by cable capacitive loading effects.

It is a further object of the present invention to provide a circuit that produces an output signal linearly related to the conductivity of the fluid.

It is a further object of the present invention to provide a measuring circuit that accurately reflects conductivity measurements down to zero, even when a grounded conductivity cell is used.

The present invention is summarized in that a conductivity measuring system includes a grounded conductivity cell and its temperature compensating resistor which are connected to the system supply and signal processing circuitry through a shielded cable; the cell end of the cable is purposely not grounded while the other end is connected to the system supply and signal processing circuitry.

BRIEF DESCRIPTION OF THE DRAWING

The drawing is a schematic circuit diagram of the preferred embodiment of the invention.

DESCRIPTION OF THE PREFERRED EMBODIMENT

The present invention is embodied in a monitoring system illustrated schematically in the drawing. A suitable AC signal (source not shown) is fed into the circuit at terminal 10 and is passed through a potentiometer 12 to circuit common 14 and back to the source through terminal 16. Fine adjustment of the AC input signal to the desired level is accomplished through movable potentiometer arm 18.

The voltage appearing at arm 18 is fed to the noninverting input 20 of a high gain integrated circuit differential amplifier IC1. The inverting input 22 of IC1 is connected through conductors 23 and 24 to the output 26 of IC1 to provide the very low source impedance that is necessary for proper operation of the following stages. Output 26 of IC1 is connected through conductor 24, junction 28 and conductor 30 to the noninverting input 32 of high gain integrated circuit differential amplifier IC2. Output 26 is connected through conductor 24 and resistors R1 and R2 to circuit common at 15. Output 26 is connected through conductors 24 and 29 directly to shield cable 52 at terminal T2-4 and, hence, to the free end of the shield cable at terminal T1-4 which is purposely not grounded. The particular shield cable shown is the three conductor type which may be of any desired length to meet the circumstances of the installation. Shield cable lengths of several hundred feet have presented no degrading of the electrical conductivity signal. IC1 (as do IC2 and IC3) has positive and negative input pins connected to a suitable DC source (not shown). IC2 has an inverting input 34 and an output 36.

A third high gain integrated circuit differintial amplifier IC3 has a noninverting input 42, an inverting input 44 and an output 46.

IC2 output 36 is connected through a resistor R5 to inverting input 34. Output 36 is also connected through resistor R6, terminals T2-1 and T1-1 of shield cable 52 and through thermistor R7 to electrode 54 of a conductivity cell and thence through the fluid 56 to the grounded electrode 58 of the conductivity cell and finally to a pipe ground at 60. The junction 62 between one end of thermistor R7 and cell electrode 54 is connected through shield cable terminals T1-2 and T2-2 to the inverting input 34 of IC2. The junction 64 between cell electrode 58 and the pipe ground 60 is connected through terminals T1-3 and T2-3 and conductor 66 to circuit common 17.

Thermistor R7 is positioned adjacent the fluid to have essentially the same temperature in order to provide automatic temperature compensation for the system by adjusting for ohmic variations of the fluid due to temperature variations. Resistors R5 and R6 function to provide the thermistor circuit with shaping to better enable the temperature response of the thermistor circuit to approximate that of the fluid. Such automatic temperature compensation techniques are well known to those skilled in the art of fluid conductivity measurements.

Output 36 of IC2 is connected through resistors R3 and R4 to the system output terminal 68. Noninverting input 42 of inverting amplifier IC3 is connected to the junction of resistors R1 and R2, while inverting input 44 of IC3 is connected to the junction of resistors R3 and R4. The output 46 of IC3 is connected to the system output 68. An appropriate meter and/or display may be connected between output 68 and circuit common 15 to provide the temperature corrected valve of the conductance of fluid 56.

IC1 functions to provide the shield cable 52 with a low source resistance which aids in the shielding of the signal. Additionally, IC1 functions to set the voltage level of IC2's inverting input 34 at the same voltage level as the shield cable 52 so that a signal being conducted along the cable is not degraded either by capacitive loading effects or poor wire insulation. Finally, IC1 provides the precision of a very low source impedance required for the proper operation of IC3's substraction mode.

The voltage appearing at the output 36 of IC2 will depend upon the ratio of thermistor resistance R7 to the resistance of the fluid 56 and the voltage supplied to the noninverting input 32. Prior to this invention the voltage at output 36 presented an error component using then known conductivity measuring techniques. Through the use of the inversion substracting feature provided by IC3, this substantial error is reduced to practically zero, which is an improvement of as much as 20 percent.

It can thus be seen that, through the disclosure of the present invention, the commonly used one-element grounded conductivity cell can be used at great distances from the reading station, with high accuracy, by using inexpensive shielded cable which provides a perfect linear output as to the conductance of the fluid.

Obviously many modifications and variations of the present invention are possible in the light of the above teachings. It is therefore to be understood that within the scope of the appended claims the invention may be practiced otherwise than as specifically described.

What is claimed is:

1. A circuit for measuring and linearly indicating the conductivity of a fluid comprising:
   a first amplifier having an output for supplying a source voltage to said circuit and providing a low source resistance to said circuit;
   a second amplifier having noninverting, inverting and output terminals; wherein said first amplifier output is connected to said second amplifier noninverting input;
   a conductivity cell having first and second electrodes, said second electrode being grounded;
   a temperature compensating resistor connected to said first cell electrode;
   a shielded cable having first, second and third conductors and a first terminal connected to one end of said cable and a second terminal connected to the other end of said cable; whereby said first amplifier output is connected to said second terminal of said cable and said first cable terminal is ungrounded, said first cable conductor being connected between one end of said thermistor and said second amplifier output, said second cable conductor being connected between said first cell electrode and said second amplifier inverting input, and said third cable conductor being connected between said second cell electrode and circuit common.

2. A conductivity measuring system in accordance with claim 1, wherein said first and second amplifiers are high gain integrated circuit differential amplifiers.

3. A conductivity measuring system in accordance with claim 1, and further comprising a third amplifier having inverting and noninverting inputs and an output terminal, said inverting input being connected to said second amplifier output and said noninverting input being connected to said second amplifier noninverting input.

* * * * *